(12) United States Patent
Påhlsson

(10) Patent No.: US 11,467,162 B2
(45) Date of Patent: Oct. 11, 2022

(54) DIAGNOSTIC TEST FOR HEPATOCELLULAR CARCINOMA

(71) Applicant: Glycobond AB, Linköping (SE)

(72) Inventor: Peter Påhlsson, Linköping (SE)

(73) Assignee: Glycobond AB, Linköping (SE)

( * ) Notice: Subject to any disclaimer, the term of this patent is extended or adjusted under 35 U.S.C. 154(b) by 918 days.

(21) Appl. No.: 16/099,240

(22) PCT Filed: May 8, 2017

(86) PCT No.: PCT/EP2017/060892
§ 371 (c)(1),
(2) Date: Nov. 6, 2018

(87) PCT Pub. No.: WO2017/194455
PCT Pub. Date: Nov. 16, 2017

(65) Prior Publication Data
US 2020/0319189 A1 Oct. 8, 2020

(30) Foreign Application Priority Data
May 9, 2016 (SE) .................................... 1650619-8

(51) Int. Cl.
*G01N 33/574* (2006.01)
*G01N 33/543* (2006.01)

(52) U.S. Cl.
CPC . *G01N 33/57438* (2013.01); *G01N 33/54306* (2013.01); *G01N 33/57488* (2013.01); *G01N 2333/42* (2013.01); *G01N 2400/02* (2013.01)

(58) Field of Classification Search
CPC ....... G01N 33/57438; G01N 33/54306; G01N 33/57488; G01N 2333/42; G01N 2400/02
See application file for complete search history.

(56) References Cited

U.S. PATENT DOCUMENTS

| 8,178,319 | B2* | 5/2012 | Påhlsson | C07K 14/37 |
| | | | | 435/69.1 |
| 2009/0317844 | A1 | 12/2009 | Riady | |
| 2017/0219590 | A1* | 8/2017 | Kuno | G01N 33/57492 |

FOREIGN PATENT DOCUMENTS

WO WO-2009/136859 A1 11/2009

OTHER PUBLICATIONS

Campbell (from Monoclonal Antibody Technology, Elsevier Sci Pub. 1984, total 16 pages) (Year: 1984).*

(Continued)

*Primary Examiner* — Changhwa J Cheu
(74) *Attorney, Agent, or Firm* — Marshall, Gerstein & Borun LLP

(57) ABSTRACT

The present invention relates to a method for detecting fucosylated alpha1-acid glycoprotein (AGP) in a sample, comprising the steps providing a monovalent fucose-binding peptide having at least 80% identity, such as 85, 90, 95, 99 or 100% identity, to a peptide having an amino acid according to SEQ ID NO: 1, immobilised on a solid phase; bringing the sample into contact with the immobilised fucose-binding peptide; and detecting any fucosylated AGP bound to said fucose-binding peptide. The invention further relates to a method for assessing a risk that a human individual suffers from hepatocellular carcinoma, and to a kit of parts and antibodies useful in the methods according to the invention, and to a peptide useful as an immunizing antigen in production of such antibodies.

20 Claims, 7 Drawing Sheets

Specification includes a Sequence Listing.

(56) References Cited

OTHER PUBLICATIONS

Tanabe J. Proteome Res. 2016 15:2935 (Year: 2016).*
Hashimoto Cancer 2004 101: 2825 (Year: 2004).*
Croce Histol. Histopathol. 2005 20: 91 Abstract Only (Year: 2005).*
Invitrogen, ORM1 Polyclonal Antibody, Product Details, downloaded from the Internet at: <https://www.thermofisher.com/antibody/product/ORM1-Antibody-Polyclonal/PA1-9530> (Jun. 24, 2015).
"Alpha-1 Acid Glycoprotein Antibody", Lot No. QF2045593 Product Data Sheet, Thermo Scientific (Jun. 24, 2015).
Ahn et al., Quantitative analysis of aberrant protein glycosylation in liver cancer plasma by AAL-enrichment and MRM mass spectrometry, Analyst, 138(21):6454-62 (Nov. 2013).
Asao et al., Development of a novel system for mass spectrometric analysis of cancer-associated fucosylation in plasma a1-acid glycoprotein, Biomed. Res. Int., 834790 (2013).
Asazawa et al., Serum fucosylated haptoglobin in chronic liver diseases as a potential biomarker of hepatocellular carcinoma development, Clin. Chem. Lab. Med., 53(1):95-102 (Jan. 2015).
Bruix et al., Management of hepatocellular carcinoma: an update, Hepatology, 53(3):1020-2 (Mar. 2011).
Chio et al., Changes in serum alpha 1 antitrypsin, alpha1 acid glycoprotein and beta 2 glycoprotein I in patients with malignant hepatocellular carcinoma, Cancer, 43(2):596-604 (Feb. 1979).
Communale et al., Total serum glycan analysis is superior to lectin-FLISA for the early detection of hepatocellular carcinoma, Proteomics Clin. Appl., 7(9-10):690-700 (Oct. 2013).
Comunale et al., Identification and development of fucosylated glycoproteins as biomarkers of primary hepatocellular carcinoma, J. Proteome Res., 8(2):595-602 (Feb. 2009).
Comunale et al., Linkage specific fucosylation of alpha-1-antitrypsin in liver cirrhosis and cancer patients: implications for a biomarker of hepatocellular carcinoma, PLoS One, 5(8):e12419 (Aug. 2010).
Ertle et al., A combination of a-fetoprotein and des-?-carboxy prothrombin is superior in detection of hepatocellular carcinoma, Digestion, 87(2):121-31 (2013).
International Application No. PCT/EP2017/060892, International Search Report and Written Opinion, dated Nov. 7, 2017.
Kaji et al., Glycoproteomic discovery of serological biomarker candidates for HCV/HBV infection-associated liver fibrosis and hepatocellular carcinoma, J. Proteome Res., 12(6):2630-40 (Jun. 7, 2013).
Kohler et al., Continuous cultures of fused cells secreting antibody of predefined specificity, Nature, 256(5517):495-7 (Aug. 1975).
Leenaars et al., The Production of Polyclonal Antibodies in Laboratory Animals. The Report and Recommendations of ECVAM Workshop 35, Altern. Lab Anim., 27(1):79-102 (Jan.-Feb. 1999).
Marrero, Hepatocellular carcinoma, Curr. Opin. Gastroenterol., 22(3):248-53 (May 2006).
Naitoh et al., Highly enhanced fucosylation of serum glycoproteins in patients with hepatocellular carcinoma, J. Gastroenterol. Hepatol., 14(5):436-45 (May 1999).
Nakagawa et al., Glycomic analysis of alpha-fetoprotein L3 in hepatoma cell lines and hepatocellular carcinoma patients, J. Proteome Res., 7(6):2222-33 (Jun. 2008).
Olausson et al., Production and characterization of a monomeric form and a single-site form of Aleuria aurantia lectin, Glycobiology, 21(1):34-44 (Jan. 2011).
Olewicz-Gawlik et al., Fucosylation of serum alpha1-acid glycoprotein in rheumatoid arthritis patients treated with infliximab, Clin. Rheumatol., 26(10):1679-84 (Oct. 2007).
Perz et al., The contributions of hepatitis B virus and hepatitis C virus infections to cirrhosis and primary liver cancer worldwide, J. Hepatol., 45(4):529-38 (Oct. 2006).
Rydén et al., Diagnostic accuracy of alpha(1)-acid glycoprotein fucosylation for liver cirrhosis in patients undergoing hepatic biopsy, Clin. Chem., 48(12):2195-201 (Dec. 2002).
Rydén et al., Lectin ELISA for analysis of alpha(1)-acid glycoprotein fucosylation in the acute phase response, Clin. Chem., 45(11):2010-2 (Nov. 1999).
Sarbah et al., Risk factors for hepatocellular carcinoma in patients with cirrhosis, Dig. Dis. Sci., 49(5):850-3 (May 2004).
Singal et al., Meta-analysis: surveillance with ultrasound for early-stage hepatocellular carcinoma in patients with cirrhosis, Aliment Pharmacol. Ther., 30(1):37-47 (Jul. 2009).
Tanabe et al., Outer arm fucosylation of N-glycans increases in sera of hepatocellular carcinoma patients, Biochem. Biophys. Res. Commun., 374(2):219-25 (Sep. 2008).
Wang et al., Novel fucosylated biomarkers for the early detection of hepatocellular carcinoma, Cancer Epidemiol. Biomarkers Prev., 18(6):1914-21 (Jun. 2009).
Wimmerova et al., Crystal structure of fungal lectin: six-bladed beta-propeller fold and novel fucose recognition mode for Aleuria aurantia lectin, J. Biol. Chem., 278(29):27059-67 (Jul. 2003).

* cited by examiner

○ Fucose    ⬡ AGP    Y Ab-058    ⌒ S2 – biotin labelled

DIAGNOSTIC TEST FOR HEPATOCELLULAR CARCINOMA

INCORPORATION BY REFERENCE OF MATERIAL SUBMITTED ELECTRONICALLY

The Sequence Listing, which is a part of the present disclosure, is submitted concurrently with the specification as a text file. The name of the text file containing the Sequence Listing is "53469_Seqlisting.txt", which was created on Oct. 31, 2018, and is 3,473 bytes in size. The subject matter of the Sequence Listing is incorporated herein by reference in its entirety.

FIELD OF THE INVENTION

The present invention relates to the field of biomarkers and assays for use in detection of biomarkers, and to antibodies useful in such assays. In particular, the invention relates to assays for detecting biomarkers indicative of primary liver cancer (hepatocellular carcinoma, HCC).

BACKGROUND

Primary liver cancer (hepatocellular carcinoma, HCC) is one of the most prevalent human cancers and the third deadliest. Most cases of HCC develop on the background of liver cirrhosis and the major etiology for developing cirrhosis and HCC is chronic hepatitis B virus (HBV) or hepatitis C virus (HCV) infection. HBV and HCV infections are associated with >80% of all HCC cases worldwide[1-3]. Non-viral background for development of HCC includes liver cirrhosis caused by alcoholic disease, diabetes and metabolic and autoimmune diseases.

If HCC tumors are detected at an early stage, curative treatment using surgical resection, transplantation or radiofrequency ablation can be offered. However, only 30% of HCC tumors are detected in an early stage, being eligible for potentially curative treatment.

The most commonly used serum biomarker to diagnose and measure progression of HCC is alpha-fetoprotein (AFP). However the diagnostic power of AFP to detect HCC is limited. Both liver cirrhosis and hepatitis can lead to elevated levels of AFP and almost half of the patients diagnosed with HCC do not show elevated levels of AFP. Another biomarker, des-gamma-carboxy prothrombin (DCP) has shown somewhat better diagnostic sensitivity than AFP in some clinical studies[4]. However, both AFP and DCP show insufficient diagnostic sensitivity and specificity to be used as screening markers and their use as diagnostic markers in surveillance is not recommended in international guidelines[5]. Ultrasound has better diagnostic sensitivity and specificity (60-80%) but suffers from high costs and inability to detect tumors at an early stage[6].

Glycosylation changes in serum glycoproteins have been shown to be associated with liver disease and the development and progression of HCC. The most well studied example is the increase in a core-fucosylated form of AFP, AFP-L3, which has shown higher specificity for HCC than using AFP alone[7].

Increases in fucosylation of plasma proteins is a common finding associated with HCC and mass spectrometry studies have revealed specific differences in fucosylation patterns between liver cirrhosis and HCC patients[8-13]. However studies using lectins such as the fucose-binding lectin from *Aleuria aurantia* (AAL), that has a broad specificity towards fucose, often shows problems in differentiating between patients with HCC and patients with liver cirrhosis[14, 15].

The fucose-binding lectin AAL has been widely used to study fucosylation changes of plasma proteins associated with disease. AAL is composed of two identical subunits, where each subunit contains five binding sites for fucose[16]. AAL displays a broad specificity for fucosylated oligosaccharides and binds to oligosaccharides with fucose linked α1-6, α1-2, α1-3 and α1-4, including sialylated and fucosylated structures such as $SLe^x$ and $SLe^a$. The five different binding sites differ in binding specificity and affinity.

Monovalent fucose-binding peptides derived from AAL are known from WO2009/136859. A recombinant form of AAL comprising only binding site 2, S2, has been produced[17]. This recombinant form showed a more restricted binding towards fucosylated oligosaccharides with reduced binding towards sialylated/fucosylated oligosaccharides compared to AAL. It also showed a general lower affinity towards fucosylated structures, with highest affinity towards multifucosylated oligosaccharides and oligosaccharides containing α1-6 linked fucose.

SUMMARY OF THE INVENTION

The present invention relates to an assay for assaying alpha1-acid glycoprotein (AGP) with a glycosylation pattern specific for primary liver cancer (hepatocellular carcinoma, HCC).

In a first aspect, the invention relates to a method for detecting fucosylated alpha1-acid glycoprotein (AGP) in a sample, comprising the steps
  providing a monovalent fucose-binding peptide having at least 80% identity, such as 85, 90, 95, 99 or 100% identity, to a peptide having an amino acid according to SEQ ID NO: 1, immobilised on a solid phase;
  bringing the sample into contact with the immobilised fucose-binding peptide; and
  detecting any fucosylated AGP bound to said fucose-binding peptide.

In a further aspect, the invention relates to a method for assessing a risk that a human individual suffers from hepatocellular carcinoma (HCC), comprising the steps of detecting fucosylated AGP in a sample from said individual using the method according to the above aspect, wherein an increased concentration of fucosylated AGP, as compared to a reference concentration derived from human individuals not suffering from HCC, indicates an increased risk that the individual suffers from HCC.

In a further aspect, the invention relates to a kit of parts comprising a monovalent fucose-binding peptide having at least 80% identity, such as 85, 90, 95, 99 or 100% identity, to a peptide having an amino acid according to SEQ ID NO: 1 immobilised to a solid phase and at least a first detection antibody capable of specific binding to a fucosylated AGP bound to said fucose-binding peptide.

The invention also relates to the use of a kit according to the invention in the methods according to the above aspects.

In further aspects, the invention relates to an isolated peptide consisting of an amino acid sequence having at least 83%, such as 88, 94 or 100% identity to the amino acid sequence according to SEQ ID NO: 3, and the use thereof in the production of antibodies. Such antibodies are useful in the methods according to the above aspects.

The invention also relates to antibodies capable of specific binding to an epitope overlapping at least in part amino acid residues 183-189 of human AGP, and to IgG antibodies capable of specific binding to an epitope overlapping at least in part amino acid residues 183-201 of human AGP.

B. Top panel: Illustration of a reversed ELISA with S2 immobilised on a solid support. Bottom panel: Measured absorbance values for samples obtained from patients with hepatocellular carcinoma (HCC), Cirrhosis and a negative and positive control.

Figure 2:
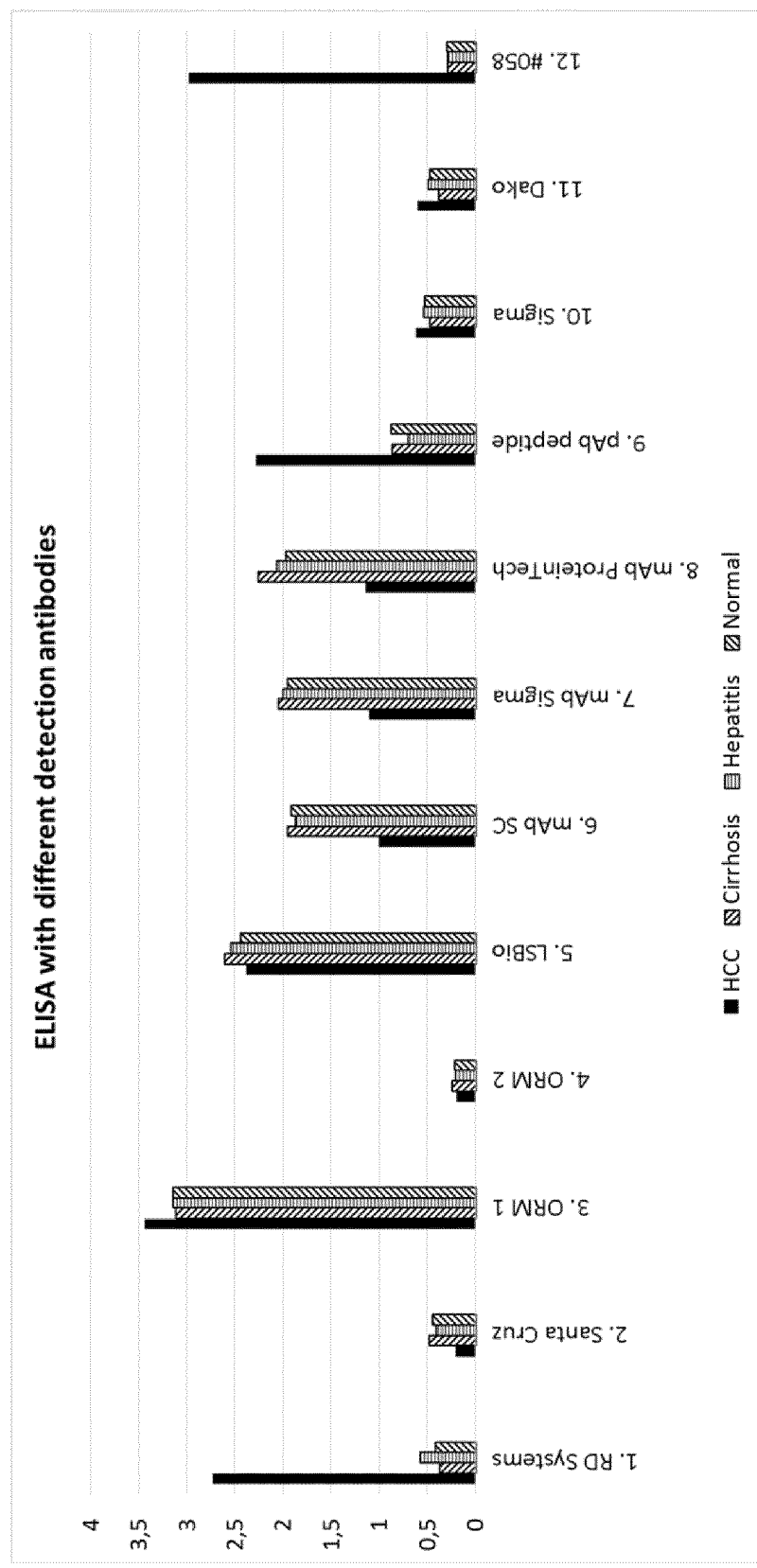

FIG. 2. Comparison of rabbit polyclonal antibody #058 and commercially available anti-AGP antibodies in reversed S2-ELISA. Analysis was performed on samples obtained from a patient with hepatocellular carcinoma (HCC), a patient with cirrhosis, a patient with hepatitis and a normal control.

Figure 3:
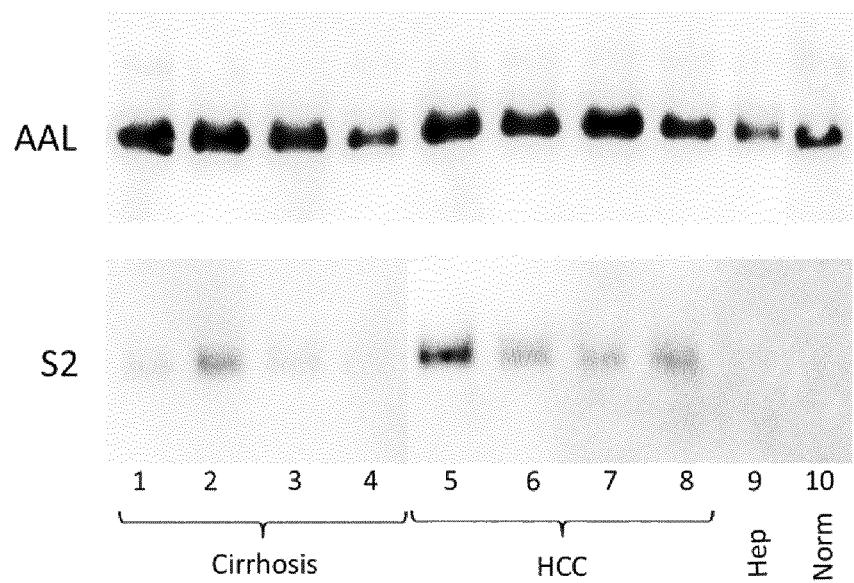

FIG. 3. Western blot analysis of AAL-enriched and S2-enriched α1-acid glycoprotein (AGP) from patient plasma samples. Lanes 1-4 represent cirrhosis samples, lanes 5-8 HCC samples, lane 9 a hepatitis sample and lane 10 a normal plasma sample. AGP was detected using the anti-human AGP antibody 058.

Figure 4:
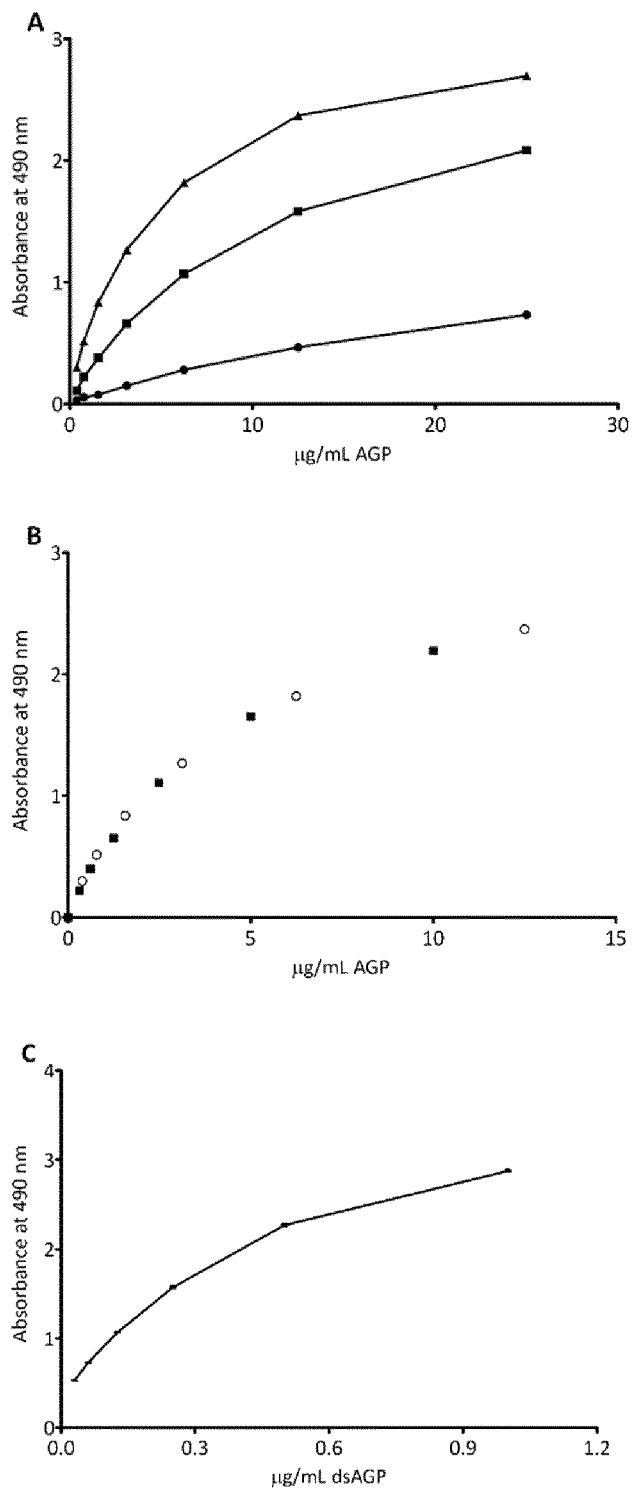

FIG. 4. A. Binding of different concentrations of purified AGP from patient samples in the reversed S2-ELISA assay. Binding of AGP from HCC (black triangles), cirrhosis (black squares) and normal sample (black circles) was analysed in the reversed S2-ELISA.

B. Analysis of Matrix effect in the reversed S2-ELISA. Binding of different concentrations of purified AGP from a HCC patient sample diluted in PBS containing 1% BSA (circles) and in normal plasma (black squares).

C. Binding of different concentrations of dsAGP in the reversed S2-ELISA assay.

Figure 5:
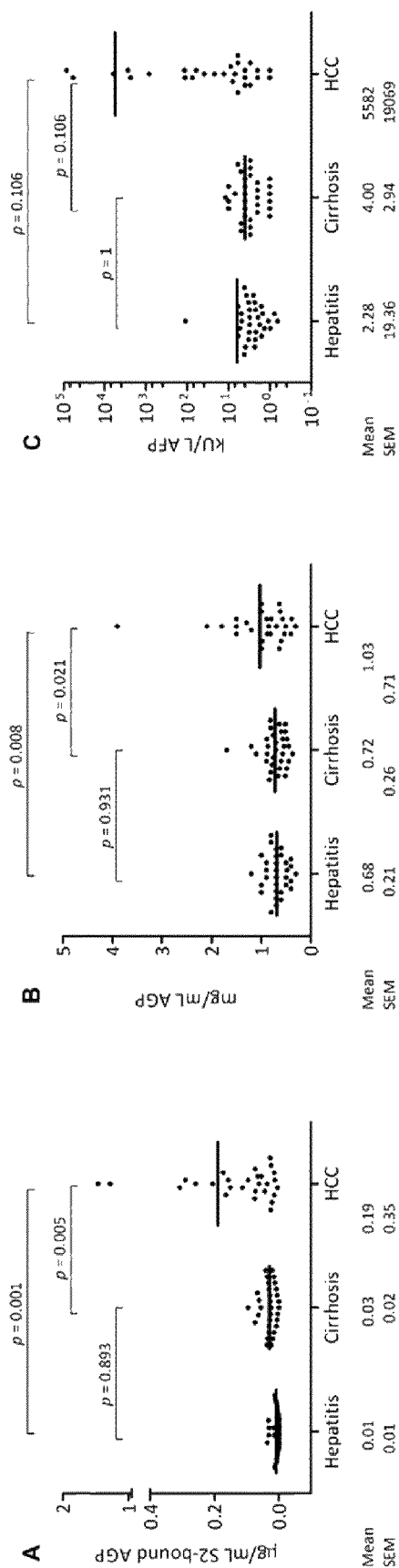

FIG. 5. Scatter plots of levels of S2-bound AGP (A), AGP (B), and AFP (C) in patients with hepatitis, cirrhosis and HCC.

Figure 6:
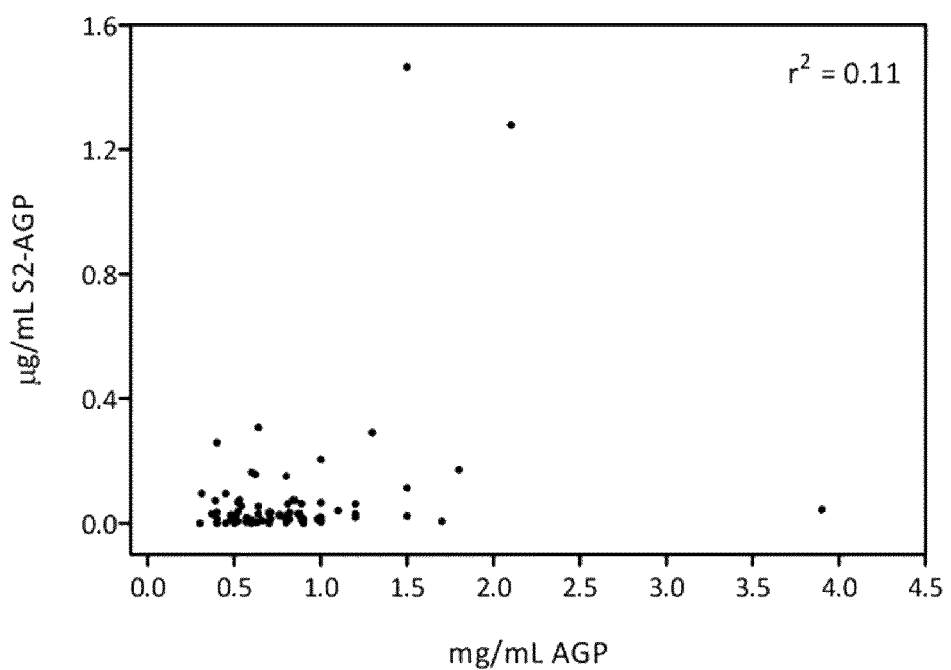

FIG. 6. Correlation plot of levels of AGP and S2-bound AGP. The r square value is 0.11.

DEFINITIONS

All terms and words used in the present specifications shall generally be construed to have the meaning generally given to them by a person skilled in the art. For the sake of clarity, a few terms are expressly defined below.

"Specificity" as used herein in relation to antibodies means the quality of an antibody to bind to a specific epitope with significantly higher affinity as compared to similar but non-identical epitopes.

"Affinity" as used herein means an attractive force between substances or particles that causes them to enter into and remain in chemical combination. Affinity designates the tendency of two substances to form strong or weak chemical bonds, forming molecules or complexes, or the thermodynamic bond strength of an antigen-antibody complex. The strength of a noncovalent binding between two substances in a complex is measured by the dissociation constant of the complex. Within immunology, affinity is a thermodynamic expression of the strength of the interaction between a single antigen binding site and a single antigenic determinant, and thus of the stereochemical compatibility between them.

"AGP" as used herein means α1-acid glycoprotein (also known as orosomucoid). AGP is a 41-43 kDa glycoprotein with a pI of 2.8-3.8. For mature human AGP the peptide moiety is a single chain of 183 amino acids with two disulfide bridges. The carbohydrate content represents 45% of the molecular weight attached in the form of five to six highly sialylated complex-type-N-linked glycans. The sequence of human AGP is provided as SEQ ID NO: 2, wherein residues 1-18 is a signal peptide not present in the mature protein. References to specific amino acid positions in AGP in the present disclosure is made using the sequence according to SEQ ID NO: 2.

"HCC" as used herein means hepatocellular carcinoma. HCC is a primary malignancy of the liver and occurs predominantly in patients with underlying chronic liver disease and/or cirrhosis. By primary malignancy, it is meant that HCC should be distinguished from metastatic liver cancer where the cancer originates from another organ and subsequently spreads to the liver via metastasis. HCC accounts for most liver cancers.

"Identity" as used herein means the extent to which two amino acid sequences have the same residues at the same positions in an alignment. Identity is expressed as a percentage. Alignment is the process or result of matching up the amino acid residues of two or more amino acid sequences to achieve maximal levels of identity and conservation. Alignments of amino acid sequences may be made by a number of available tools, such as Clustal Omega available on the website of the European Bioinformatics Institute, http://www.ebi.ac.uk/Tools/msa/clustalo/.

Peptides having at least 80% identity, such as 85, 90, 95, 99 or 100% identity, to a peptide having an amino acid according to SEQ ID NO: 1 are collectively referred to as "S2" or "52-peptide" in the present disclosure.

Sequences

SEQ ID NO: 1 is the amino acid sequence of a recombinant form of *Aleuria aurantia* lectin (AAL) comprising only binding site 2.

SEQ ID NO: 2 shows the sequence of human alpha1-acid glycoprotein (AGP).

SEQ ID NO: 3 shows amino acid residues 183-201 of human alpha1-acid glycoprotein (AGP).

DETAILED DESCRIPTION OF THE INVENTION

The present inventors have identified that a monovalent fucose-binding peptide having the amino acid sequence according to SEQ ID NO: 1, below denoted S2-peptide, shows binding characteristics that are useful in assaying the presence of α1-acid glycoprotein (AGP) having a glycosylation pattern indicative of hepatocellular carcinoma.

Lectin agarose bead precipitation was used to analyze whether there was a difference in the amount of AAL-bound AGP in plasma from patients with hepatitis, cirrhosis and HCC. There was an increase in AAL bound AGP in both the cirrhosis and HCC patient samples compared to normal which is consistent with an increase in fucosylation. However, when immunoprecipitation was performed using the S2-peptide, there was a tendency that HCC-patients had an increased level of lectin bound AGP in their plasma as compared to both cirrhosis patients and hepatitis patients.

Thus, in a first aspect, the invention relates to a method for detecting fucosylated alpha1-acid glycoprotein (AGP) in a sample, comprising the steps providing a monovalent fucose-binding peptide having at least 80% identity, such as 85, 90, 95, 99 or 100% identity, to a peptide having an amino acid according to SEQ ID NO: 1 (S2-peptide), immobilised on a solid phase;

bringing the sample into contact with the immobilised fucose-binding peptide;

detecting any fucosylated AGP bound to said fucose-binding peptide.

The solid phase may be of any type useful in biological assays. Presently preferred embodiments include polystyrene microtiter plates and agarose beads having streptavidin covalently attached. Other types of solid supports include gel matrices, cellulose and nitrocellulose matrices, gel beads, magnetic beads, plastic (e.g. polystyrene) beads, and flat substrates (slides). The S2-peptide can be immobilised to the solid phase using standard technology.

When using a solid phase composed of polystyrene, the S2-peptide can be immobilised by passive adsorption as known in the art and described in the examples. The S2-peptide can also be reversibly immobilised on the solid phase, for instance by biotinylating the S2-peptide, as also described in the examples, and using a solid phase having covalently attached streptavidin moieties.

The monovalent fucose-binding peptide, when not being 100% identical to a peptide having an amino acid according to SEQ ID NO: 1, preferably shows essentially the same or higher affinity for fucosylated AGP having a glycosylation pattern indicative of hepatocellular carcinoma as the peptide having an amino acid sequence according to SEQ ID NO: 1, under the conditions disclosed in Example 1.

The sample used in the method is preferably a plasma, serum or blood sample. The sample is preferably from a human individual suspected of suffering from HCC. The sample is brought into contact with the S2-peptide immobilised on the solid support under conditions suitable for allowing fucosylated AGP optionally present in the sample to bind to the S2-peptide. Exemplary conditions are provided in the examples.

In one embodiment, the detection of any bound fucosylated AGP is performed by bringing any bound fucosylated AGP in contact with a first detection antibody capable of specific binding to a fucosylated AGP bound to said fucose-binding peptide.

In one embodiment, the first detection antibody is detected by use of a second detection antibody showing specificity for the first detection antibody. For instance, if the first detection antibody is an polyclonal IgG antibody raised in a certain species, the second detection antibody may be an antibody raised against IgG antibodies from this species, as commonly used in the art. In this embodiment, the second detection antibody is conjugated with a detectable label.

The detectable labels used in the above embodiments may be any detectable label suitable in the chosen assay format, and includes without limitation enzymes, including horseradish peroxidase, alkaline phosphatase and glucose oxidase; and fluorophores.

In one embodiment, the S2-peptide is reversibly immobilised to the solid phase. The detection of any bound fucosylated AGP may then be performed by releasing the S2-peptide from the solid phase and eluting the S2-peptide along with any fucosylated AGP bound to the S2-peptide or releasing fucosylated AGP from the S2-peptide. Fucosylated AGP can then be detected and optionally quantified in the eluate.

In a further aspect, the invention relates to a method for assessing a risk that a human individual suffers from hepatocellular carcinoma (HCC), comprising the steps of detecting fucosylated AGP in a sample from said individual using the method as described above, wherein an increased concentration of fucosylated AGP, as compared to a reference concentration derived from human individuals not suffering from HCC, indicates an increased risk that the individual suffers from HCC.

As for the previous aspect, the sample is preferably a blood, serum, or plasma sample.

In one embodiment of this aspect, the invention further comprises measuring one or both of total AGP concentration and total alpha-fetoprotein (AFP) concentration in the sample. Assays for total AGP and total AFP are commercially available from a number of suppliers, e.g. Fujirebio Diagnostics, Inc., R&D Systems, Inc., and LifeSpan BioSciences, Inc. Using a combination of these one or two additional biomarkers enables an even better differentiation between HCC on the one side and cirrhosis and hepatitis on the other side, as compared to measurement of only fucosylated AGP binding to S2-peptide.

In a further aspect, the invention relates to a kit of parts for performing the methods according to the invention. Such a kit preferably comprises a monovalent fucose-binding peptide having at least 80% identity, such as 85, 90, 95, 99 or 100% identity, to a peptide having an amino acid according to SEQ ID NO: 1 immobilised to a solid phase and at least a first detection antibody capable of specific binding to a fucosylated AGP bound to said fucose-binding peptide.

The first detection antibody may be conjugated to a detectable label, or the kit may comprise a second detection antibody capable of specific binding to the first detection antibody, and wherein the second detection antibody is conjugated to a detectable label. The detectable labels are as disclosed above.

In one embodiment, the method used for detecting the fucosylated alpha1-acid glycoprotein (AGP) in the sample is embodied in a reversed ELISA.

ELISA (Enzyme-linked immunosorbent assay) is a well-known method for detecting and quantifying a component from an analytical mixture, such as serum, and was first described in 1971. Since then, the method has been further developed and is widely used. Apart from the direct ELISA, there are three variations commonly used; indirect ELISA, Sandwich ELISA and Competitive ELISA. An extensive disclosure of ELISA analysis and standard protocols can be found on the website ELISA encyclopedia (http://www.elisa-antibody.com/)

In general, an ELISA analysis comprises the following steps. All washing steps during the entire ELISA procedure is done with a buffered solution. The buffered solution is preferably a phosphate-buffered saline solution comprising Tween (PBST).

Solid support preparation: The solid support is coated by passive adsorption of an antigen or a capture antibody to the solid support. The material for the solid is usually polystyrene, and usually a tube or microtiter plate of polystyrene is used. Preferably, a 96 well microtiter plate (microplate) is used.

The antigen or antibody is immobilized to the solid support by passive adsorption to the polystyrene surface. This is usually performed during a prolonged time period, such as overnight, at 4° C. Alkaline conditions are preferred for the immobilisation step, although coating at pH 7 may for some applications be acceptable. After the immobilisation step, the solid support is washed and normally blocked with a protein to inhibit immobilization of any other unknown molecules to the solid support which may influence the analysis. The blocking is usually preformed by using Bovine Serum Albumin (BSA) in a phosphate-buffered saline (PBS) solution. After blocking, the solid support is washed.

Assay procedure: The sample to be tested, in liquid form, is added to the solid support and thereafter incubated. Any antibody or antigen with an affinity or specificity for the antigen or capture antibody immobilized on the solid support, will bind thereto. The liquid sample is removed, and the solid support washed to remove any unbound molecules.

Thereafter at least one detection antibody is added, which may be polyclonal or monoclonal. It may be a first detection antibody binding to the antigen from the test sample, followed by a second detection enzyme-conjugated antibody, directed against the first detection antibody. If an antibody from the test sample is bound to an antigen on the solid support, an enzyme-conjugated second detection antibody may be directly added for detection.

As second detection antibody, normally IgG immunoglobulins are used, having a specificity for the antibody from the sample, or for the first detection antibody. If for instance the first detection antibody is from rabbit, the second detection antibody will be anti-rabbit. This second detection antibody has an enzyme conjugated thereto. A number of enzymes have been employed for this purpose including alkaline phosphatase (AP), horseradish peroxidase (HRP), glucose oxidase and p-nitrophenyl phosphatase. Commercially available conjugates are prepared using a glutaraldehyde coupling method with peroxidase. Instead of an antibody, the secondary reagent may however relate to any other molecule that may specifically bind to the antigen, and be conjugated to the enzyme, as long as it is suitable for use in an ELISA analysis. This may for instance be a fluorophore.

After adding the antibody, and between the addition of a first and second detection antibody, the solid support is again washed.

Thereafter a substrate solution is added and the solid support allowed to incubate for a period of time. The substrate will cause the enzyme to generate a colored reaction product. The time required will depend on the enzyme and substrate combination chosen for the detection.

The substrates that may be used for causing the enzymes above to generate a colored reaction product differ depending on the enzyme used. 4-Nitrophenylphosphate is the substrate commonly used for AP. Commonly used substrates with HRP are 5-aminosalisylic acid, 3,3'-diaminobenzidine, 2,2'-Azinobis[3-ethylbenzothiazoline-6-sulfonic acid]diammonium salt, o-phenylenediamine dihydrochloride, 3,3'.5.5'-tratramethylbenzidine. The substrate used with p-nitrophenyl phosphatase is normally p-Nitrophenyl phosphate disodium.

After the required period of time has passed, a stop solution is added to stop the reaction. Immediately thereafter, the measurement of the colored reaction product is detected by measuring the intensity of transmitted light, or the optical density, from the product, by spectrophotometry. The reading is preferably done with a microplate reader. The detection of the reaction product may be chromogenic, chemifluorescent or chemifluorescent, depending on the enzyme and substrate used.

Substrates are commercially available and the person skilled in the art may easily prepare the substrate solutions depending on the enzyme conjugated to the detection antibody. Microplate readers are also readily commercially available.

Calculation of the results: Using a mean zero standard absorbance, which is included in the analysis, the mean absorbance for each well or tube is calculated. The mean absorbance is plotted in a standard curve against concentration.

Figure 1A:
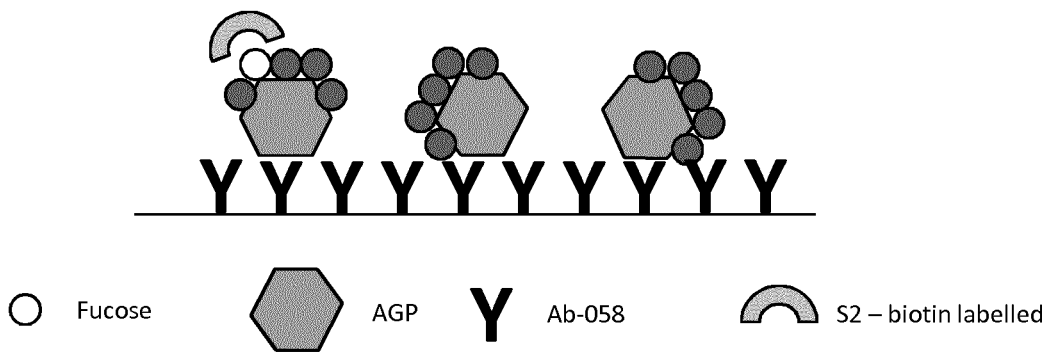
FIG. 1. A. Top panel: Illustration of a standard ELISA with antibody #058 immobilised on a solid support. Bottom panel: Measured absorbance values for samples obtained from patients with hepatocellular carcinoma (HCC), Cirrhosis and a negative and positive control.
Figure 1A:
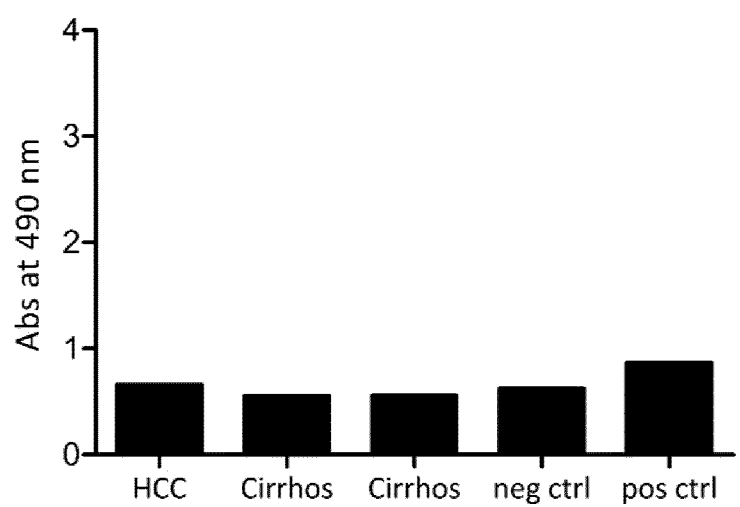

The inventors have constructed a standard ELISA wherein a first detection antibody has been immobilized on the microplate, as an antigen detecting agent (see FIG. 1A). The first detection antibody used has been an antibody directed against the human plasma derived α1-acid glycoprotein (AGP). Thereafter the solid support has been incubated with the patient plasma sample. Any α1-acid glycoprotein present in the patient plasma sample is then bound to the first detection antibody. Thereafter, a monovalent fucose-binding peptide, conjugated with biotin is added. The biotin conjugated fucose-binding peptide will bind to and detect any AGP that is fucosylated, using streptavidin coupled to alkaline phosphatase as the enzyme and pNPP substrate in Tris-buffer for detection (See FIG. 1A).

However, this standard ELISA did not provide a satisfactory signal to background ratio.

Figure 1B:
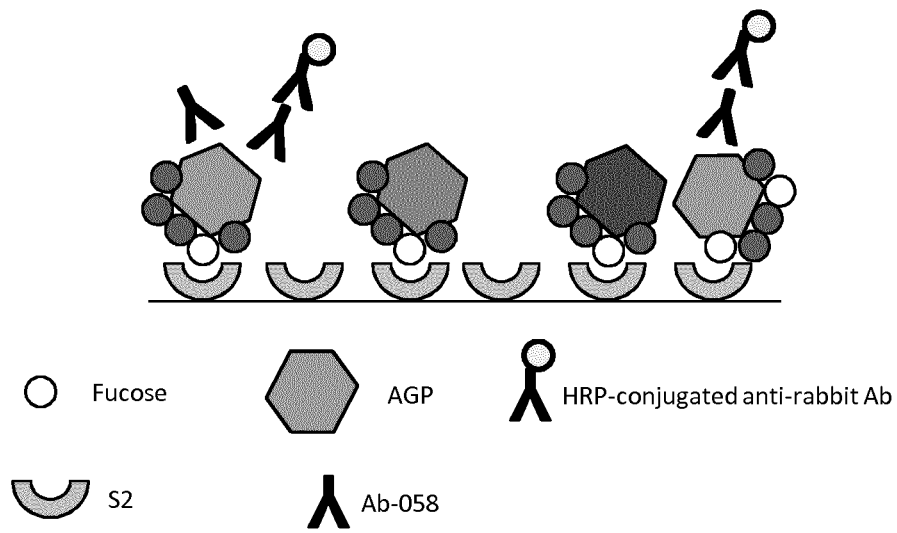
Figure 1B:
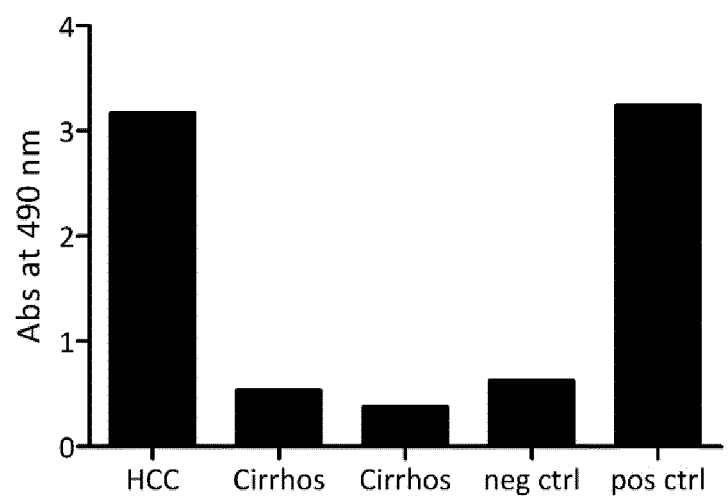

The inventors therefore developed the methods according to the invention, of which one preferred embodiment is schematically disclosed in FIG. 1B top panel, where the signal to noise ratio was drastically improved. This can be seen by comparing the results provided in the bottom panels of FIG. 1A and FIG. 1B, respectively. Instead of immobilising the antibody directed against the human plasma derived AGP to the solid support, the S2-peptide is immobilized on the solid support. By doing so, only fucosylated proteins will bind to the solid support when said support is incubated with the patient plasma sample. Thereafter, the first detection antibody directed against the human plasma derived AGP is added, so that the first detection antibody will bind to any AGP bound to the S2-peptide that is adsorbed onto the solid support. Finally, to be able to detect the AGP bound to the S2-peptide, a HRP-conjugated second detection antibody directed against the first detection antibody is added. Thereafter detection is performed as is standard procedure for ELISA analysis. This model is referred to as the S2-reversed ELISA.

In one aspect, the invention relates to a method for producing antibodies, characterized in that a peptide consisting of an amino acid sequence having at least 83%, such as 88, 94 or 100% identity to the amino acid sequence according to SEQ ID NO: 3 is used as an immunogen. Such antibodies show specificity for an epitope located in the C-terminal part of human AGP and are useful as first detection antibodies in the methods and kits according to the present invention.

In one aspect, the present invention also relates to a peptide consisting of an amino acid sequence having at least 83%, such as 88, 94 or 100% identity to the amino acid sequence according to SEQ ID NO: 3, and to its use as an immunizing antigen in production of antibodies.

The antibodies produced and used in the method in the present application may be monoclonal antibodies or polyclonal antibodies.

Monoclonal antibodies represent a population of antibodies that recognize a single epitope within an antigen. They are typically produced from a single B cell of an immunized mammal, thereby generating a clonal population of antibodies, identical to one another and all recognizing the same epitope of a specific antigen. The production of monoclonal antibodies was first described by Köhler and co-workers[18]. In principle, the method comprises the steps below.

A mammal is immunized with an antigen of interest, so that the mammal will develop antibodies against said antigen. This is followed by a secondary and tertiary injection to boost the immune response and produce higher titers of antibody against the particular immunizing antigen The mammal may be for instance a rabbit, a mouse, a rat, a guinea pig, a hamster, a sheep, a goat or a horse. Following the injections, blood is collected from the spleen, and antibody-producing B-cells are isolated. Although B cells can be used to harvest antibodies, the disadvantage is that these cells have a finite lifespan and will eventually stop producing the antibody.

By fusing a specific antibody-producing B cell with a myeloma cell, a hybridoma cell is formed, thus the limited lifespan of a B cell can be overcome. The fusion of the B-cell and the myeloma cell may be done by using polyethylene glycol, a virus, or by electroporation of the cell culture comprising both cell types. After the fusion, a selection for the hybridomas must be done. This is done by using HGPRT, hypoxanthine-guanine phosphoribosyl transferase, an enzyme involved in the synthesis of nucleotides from hypoxanthine. The myeloma cells are HGPRT− and the B cells are HGPRT+. The culture is grown in HAT (hypoxanthine-aminopterin-thymine) medium, which can sustain only HGPRT+ cells. The myeloma cells that fuse with another myeloma cell or do not fuse at all die in the HAT medium since they are HGPRT−. The B cells that fuse with another B cell or do not fuse at all die because they do not have the capacity to divide indefinitely. Only hybridomas between B cells and myeloma cells survive, being both HGPRT+ and cancerous.

The initial collection of B cells from the mammal used is heterogenous, i.e. they do not all produce the same antibody. Therefore the hybridoma population does not produce a single antibody. Each hybridoma is therefore cultured and screened with methods well known within the art and familiar to the person skilled in the art. Once a certain hybridoma is detected, producing the right antibody, that immortalized B cell-myeloma hybridoma can provide a constant supply of highly specific monoclonal antibody. Since monoclonal antibodies only recognize one epitope, they generally have low cross-reactivity with non-specific antigens.

Polyclonal antibodies represent a population of antibodies collected from multiple B cell clones that have been activated by the immune response of one single immunized animal. Traditionally, a mammal, such as a goat, sheep, mouse or rabbit, is injected with a specific antigen of interest that elicits a primary immune response. This is followed by a secondary and tertiary injection that produces higher titers of antibody against the particular immunizing antigen. Serum containing the antibodies is collected from the mammal and typically affinity purified in order to enrich for the antibodies raised against the antigen in question. This process leads to the production of high titer, high affinity polyclonal antibodies against all epitopes of the antigen of interest. The production of polyclonal antibodies has been described for instance by Marlies Leenaars and co-workers[19].

EXAMPLES

The following examples are included to further illustrate the invention and are not to be construed as limiting the scope of the invention, which is that of the appended claims.

Example 1, Comparison of Standard ELISA and Reversed ELISA

Patient Samples

Plasma samples from one patient with HCC och two patients with cirrhosis were obtained from Karolinska University Hospital at Huddinge, Sweden. Normal control was a plasma pool from healthy blood donors. Positive control was dsAGP at a concentration of 2 µg/ml.

Production of Antibodies

Production of the polyclonal anti-human α1-acid glycoprotein antibody 058 was done by Agrisera antibodies (Vännäs, Sweden). Shortly, a synthetic peptide corresponding to the C-terminal amino acids 183 to 201 of human α1-acid glycoprotein was synthesized by Agrisera. The peptide was conjugated to KLH via its terminal cysteine using a maleimide crosslinker and rabbits were immunized four times with the KLH-conjugated peptide. Anti-AGP antibodies were purified from sera using the synthetic peptide coupled to 2 mL of UltraLink Iodoacteyl resin (Pierce, Rockford, Ill., USA).

Standard Lectin ELISA

Microtiter plates (Maxisorp, Nunc) were coated with Antibody 058 at 10 µg/mL in 0.05 M carbonate-bicarbonate buffer, pH 9.6 (Medicago), overnight at 4° C. Wells were blocked with 3% BSA in PBS (Medicago) for 1 h. Plates were washed 3 times with PBS+0.05% Tween 20 (PBST) before the patient plasma samples, diluted 1:50 in PBS containing 1% BSA, were added and incubated shaking at 200 rpm for 1 h. After washing the wells as above biotinylated S2-peptide was added at 0.25 µg/mL in PBS containing 1% BSA, and incubated for 1 h with gentle shaking at room temperature (RT). Bound S2-peptide was detected using a alkaline phosphatase conjugated Extravidine and pNPP substrate (Sigma-Aldrich). The amount of bound S2-peptide was measured after 30 min at 490 nm using a VERSAmax microplate reader (Molecular Devices Corporation).

Reversed S2-ELISA

Microtiter plates (Maxisorp, Nunc) were coated with S2 at 5 µg/mL in 0.05 M carbonate-bicarbonate buffer, pH 9.6 (Medicago), overnight at 4° C. Wells were blocked with 3% BSA in PBS (Medicago) for 1 h. Plates were washed 3 times with PBS+0.05% Tween 20 (PBST) before the patient plasma samples, diluted 1:50 in PBS containing 1% BSA, were added and incubated shaking at 200 rpm for 1 h. After washing the wells as above the rabbit anti-human-α1 acid glycoprotein 058 at 1 µg/mL in PBS containing 1% BSA was added and incubated for 1 h with gentle shaking at room temperature (RT). Bound anti-human-α1 acid glycoprotein was detected using a horseradish peroxidase conjugated goat anti-rabbit IgG (Jackson ImmunoResearch Laboratories, West Grove, Pa.) and O-phenylenediamine di-hydrochloride substrate (Sigma-Aldrich). The reaction was stopped after 30 minutes with addition of 25 µL/well of 1 M H2SO4 and the amount of bound anti-AGP was measured at 490 nm using a VERSAmax microplate reader (Molecular Devices Corporation).

Results

The results for standard ELISA are shown in FIG. 1A and for reversed ELISA in FIG. 1B. The reversed ELISA showed higher signal intensities compared to the standard ELISA. The signal to background ratio in the standard ELISA for a HCC sample and a positive control sample was 1.05 and 1.38, respectively, whereas the signal to noise ratio for the same HCC sample and the same positive control was improved to 5.1 and 5.2, respectively (FIG. 1).

Example 2, Comparison of Detection Antibodies

Patient Samples

The analyses were performed on plasma samples from one patient with HCC, one patient with cirrhosis, one patient with hepatitis and a plasma pool from healthy blood donors (Normal).

Assay

The reversed S2-ELISA (as exemplified above) was used to compare commercial anti-AGP antibodies with Ab-058. The 058 antibody (sample 12 in FIG. 2) was compared to a number of commercial polyclonal or monoclonal anti-AGP antibody according to the list below.

Detection Antibodies

The following antibodies were used for detection.

1. Human α1-acid Glycoprotein antibody (R&D Systems, cat no AF3694)
   Source: Polyclonal Goat IgG
   Immunogen: Human plasma derived α1-acid glycoprotein
2. Human α1-acid Glycoprotein antibody (AGP-1/2, Santa Cruz Biotechnology, cat no sc-51018)
   Source: Polyclonal Goat IgG
   Immunogen: peptide mapping within an internal region of AGP-1 of human origin
3. ORM 1 Polyclonal antibody, human and mouse spec. (ProteinTech, cat no 16439-1-AP)
   Source: Polyclonal Rabbit IgG
   Immunogen: Ag9758, Orosomucoid 1
4. ORM 2 Polyclonal antibody, human spec. (ProteinTech, cat no 11199-1-AP)
   Source: Polyclonal Rabbit IgG
   Immunogen: Ag1667, Orosomucoid 2
5. Anti-ORM 1/Orosomucoid antibody (LSBio, cat no LS-C292722)
   Source: Polyclonal Rabbit IgG
   Immunogen: recombinant human α1-AGP (aa19-201) produced in *E. coli*
6. Human α1-acid Glycoprotein antibody (AGP-1 (29A1), cat no sc-69753)
   Source: Monoclonal Mouse IgG
   Immunogen: purified α1-AGP of human origin
7. Monoclonal anti-ORM 1 antibody, clone 2F9-1F10 (Sigma, cat no WH0005004M1-100 μg)
   Source: Monoclonal Mouse IgG
   Immunogen: ORM 1 (AAH26238, 18 a.a.-202 a.a.) full length recombinant protein with GST-tag
8. ORM 1 Monoclonal Antibody, human spec. (ProteinTech, cat no 66097-1-Ig)
   Source: Monoclonal Mouse IgG
   Immunogen: Ag19248, Orosomucoid 1α
9. Human cd-Acid Glycoprotein Antibody (Thermo Scientific, cat no PA1-9530)
   Source: Polyclonal Chicken IgY
   Immunogen: Mixture of synthetic peptides corresponding to residues 149-160 and 190-201 of human α1-acid glycoprotein
10. Human α1-acid Glycoprotein antibody (Sigma, cat no A-0534)
    Source: Polyclonal Rabbit IgG
    Immunogen: purified human α1-acid glycoprotein
11. Human α1-acid Glycoprotein antibody (Dako, cat no C10326)
    Source: Polyclonal Rabbit IgG
    Immunogen: purified human α1-acid glycoprotein
12. Human α1-acid glycoprotein, affinity purified #058 (Agrisera)
    Source: Polyclonal Rabbit IgG
    Immunogen: synthetic peptide CEP 19 corresponding to aa 183-201

Results

The results are shown in FIG. 2. These results indicate that different detection antibodies differ in signal to background ratio and performance in differentiating HCC from non-HCC samples. Only the 058 antibody (no. 12) and the polyclonal IgG antibodies from R&D Systems (no. 1), and to a lesser extent also the polyclonal IgY antibody from Thermo Scientific (no. 9), show selectivity for differentiating the HCC sample from non-HCC samples, whereas other antibodies do not show such selectivity. However The 058 antibody showed somewhat better signal to background ratio compared to the polyclonal IgG antibodies from R&D Systems.

It is hypothesized that the primary detection antibodies in assays no. 1, 9, and 12 have affinity for an epitope located in the unglycosylated C-terminal part of AGP. This epitope may be available for binding when AGP with a glycosylation pattern indicative of hepatocellular carcinoma is bound to the S2-peptide, but not available to the same extent when AGP has a glycosylation pattern originating from cirrhosis, hepatitis, or a normal glycosylation pattern originating from an individual not affected by HCC, cirrhosis or hepatitis. Furthermore, several of the tested antibodies show, in contrast to 058, a high background staining indicating non-specific binding of antibody directly to coated S2, which limits their use in the reversed S2-ELISA.

Example 3, Validation of Reversed S2-ELISA Using Purified AGP Samples

Purification of AGP

AGP was isolated from plasma samples using a two-step ion exchange chromatography method according to Asao et al.[20]. One mL plasma samples were applied to a HiTrap Desalting column (GE Healthcare, Uppsala, Sweden) equilibrated with 20 mM citrate-phosphate buffer, pH 4. The desalted peak was applied to a HiTrap DEAE column (GE Healthcare) equilibrated with 20 mM citrate-phosphate buffer, pH 4. Fractions containing AGP were eluted with 20 mM citrate-phosphate buffer, pH 7, containing 200 mM NaCl, pooled and applied on two joined HiTrap Desalting columns equilibrated with 20 mM citrate-phosphate buffer, pH 4. The desalted peak was applied to a HiTrap SP column (GE Healthcare) equilibrated with 20 mM citrate-phosphate buffer, pH 4, and AGP was eluted with 20 mM citrate-phosphate buffer, pH 4.8. The eluted fractions were dialyzed against water and lyophilized.

Production of Polyclonal Anti-Human-α1 Acid Glycoprotein 058

Production of the polyclonal anti-human α1-acid glycoprotein antibody 058 was done by Agrisera antibodies (Vännäs, Sweden) as described in Example 1.

Production of Desilylated AGP (dsAGP)

AGP (1.7 mg, Sigma) was dissolved in 0.3 ml of 50 mM sodium acetate buffer, pH 5.5. Neuraminidase (60 mU, *Clostridium perfringens*, Type V, Sigma) was added and the sample was incubated at 37° C. for 4 h. Desialylated AGP was purified using affinity chromatography on a 5 ml column (NHS activated HighTrap, Amersham Biosciences) with 5 mg of immobilized anti-AGP antibody (DAKO, A0011). Chromatography was performed on ÄKTA Prime equipment (GE Healthcare). The sample was diluted to 1.3 ml with PBS, pH 7.4 (Medicago, Uppsala, Sweden) and injected on the column. After washing with PBS for 20 min (flow rate 5 ml/min) dsAGP was eluted with 0.1M glycine-HCl buffer pH 2.5. Elution was monitored by UV absorbance at 260 nm. Positive fractions were pooled and dialyzed against three changes of 2 L of milli-Q water. The dialysed dsAGP was then lyophilized.

Enrichment of S2-Binding and AAL-Binding Glycoproteins from Plasma Samples

S2-peptide and recombinant AAL were biotinylated using EZ-Link Sulfo NH-LC Biotinylation kit (Pierce, Rockford, Ill., USA) according to the manufacturer's protocol. A 5 molar fold excess of biotin reagent per protein sample was used for the biotinylation. The biotin/protein ratio was determined using a HABA/avidin-assay and calculated to 1 biotin moiety per S2 molecule and 2 biotin moieties per AAL molecule. EZview Red Streptavidin Affinity Gel (Sigma-Aldrich, Saint Louis, Mo., USA) was used for the enrichment of S2 and AAL-binding glycoproteins from plasma samples according to the manufacturer's protocol. Briefly, 20 µL of EZview Red Streptavidin Affinity Gel, equilibrated with phosphate buffered saline (PBS) pH 7.4 (Medicago, Uppsala, Sweden), were mixed with 10 µg of S2 or AAL and incubated for one hour at room temperature. The lectin gel was washed once with PBS, once with 3% bovine serum albumin (BSA) (Sigma-Aldrich) in PBS and three times with PBS before 1 µL of plasma sample was added. After one hour of incubation the lectin-gel was washed and mixed with Laemmli sample buffer (Bio-Rad, Hercules, Calif., USA). The enriched glycoproteins were separated under denaturing conditions on a gradient (4-20%) Miniprotean TGX gel (Bio-Rad) and transferred to a PVDF membrane for Western blot analysis. The membrane was blocked for 1 h with 3% BSA in PBS and incubated with rabbit anti-human-α1 acid glycoprotein 058 at 1 µg/mL in 3% BSA in PBS, followed by a goat anti-rabbit IgG HRP-conjugated antibody diluted 1:20000 in 1% BSA in PBS. ECL substrate (GE Healthcare, Buckinghamshire, UK) was used for the detection of enriched AGP.

Reversed S2-ELISA

Microtiter plates (Maxisorp, Nunc) were coated with S2-peptide at 5 µg/mL in 0.05 M carbonate-bicarbonate buffer, pH 9.6 (Medicago), overnight at 4° C. Wells were blocked with 3% BSA in PBS (Medicago) for 1 h. Plates were washed 3 times with PBS+0.05% Tween 20 (PBST) before the purified AGP samples, diluted in PBS containing 1% BSA, were added and incubated shaking at 200 rpm for 1 h. After washing the wells as above the rabbit anti-human-α1 acid glycoprotein 058 at 1 µg/mL in 1% BSA in PBS was added and incubated for 1 h with gentle shaking at room temperature (RT). Bound anti-human-α1 acid glycoprotein was detected using a horseradish peroxidase conjugated goat anti-rabbit IgG (Jackson ImmunoResearch Laboratories, West Grove, Pa.) and 0-phenylenediamine di-hydrochloride substrate (Sigma-Aldrich). The reaction was stopped after 30 minutes with addition of 25 µL/well of 1 M $H_2SO_4$ and the amount of bound anti-AGP was measured at 490 nm using a VERSAmax microplate reader (Molecular Devices Corporation).

Results

Recombinant full-length *Aleuria aurantia* lectin (AAL) was bound to agarose beads as described above and used to capture fucosylated glycoforms in plasma samples from four patients with HCC, four patients with cirrhosis, two patients with chronic hepatitis and from a pool of normal plasma. The captured glycoproteins were analyzed by Western blot using antibody 058.

AGP was detected in all patient samples and the normal control. However more AAL-bound AGP was detected in the samples from HCC patients and cirrhosis samples compared to the hepatitis samples and normal control. There was no visible difference between the amount of AAL-bound AGP between cirrhosis and HCC samples. (FIG. 3, top panel).

When S2-peptide was used to enrich plasma glycoproteins from the same samples, there was very little or no visible AGP staining in the normal sample and the hepatitis samples. Furthermore, in contrast to native AAL, S2 bound more AGP in the HCC samples compared to the cirrhosis samples. The cirrhosis samples showed no or moderate staining of S2-bound AGP whereas all samples from HCC patients showed staining of S2-bound AGP, indicating that S2 may be more specific towards HCC glycosylation (FIG. 3, bottom panel).

AGP was purified as described above from one patient with HCC, one patient with cirrhosis and from the normal pool and a reversed S2-ELISA was used to measure the binding of AGP. S2-peptide was coated to microtiter wells and increasing concentrations of purified AGP samples was measured using the 058 antibody as described above.

There was a dose-dependent increase in signal from all three samples. However AGP isolated from the normal pool showed very low absorbance values in the reversed S2-ELISA consistent with the lectin precipitation data. The sample from the cirrhosis patient showed intermediate absorbance values whereas AGP purified from the HCC patient (HCC-AGP) showed high absorbance values. Thus the analysis indicated that the reversed S2-ELISA may specifically detect glycosylation differences between the different samples (FIG. 4A).

The reversed S2-ELISA was further validated using a normal plasma sample with addition of purified HCC-AGP to assess matrix effects. Using a plasma dilution of 1:50 of a normal plasma sample the background signal was the same as a control sample where plasma was omitted from the assay (OD=0.2). This indicates that essentially no AGP from a normal plasma sample bound to S2-peptide. Addition of HCC-AGP to a normal plasma sample in increasing concentrations showed a dose dependent increase in absorbance which correlated with the increase in absorbance seen with samples without added plasma. This indicates that an increase in S2-bound AGP could be accurately measured in a plasma sample (FIG. 4B).

To optimize the coating concentration of S2 and the dilution of first and second detection antibodies in the reversed lectin assay, absorbance values were measured for a HCC-plasma sample and a normal sample (background) using different coating and antibody concentrations. It was found that a coating concentration of 5 µg/ml S2, first detection antibody concentration of 1:200 and second detection antibody concentration of 1:40 000 gave an optimal signal to background ratio of over 10 (data not shown).

A standard curve was constructed using a desialylated form of AGP (dsAGP). In contrast to the normal sialylated form of AGP, S2 will have an affinity towards the exposed terminal $Le^x$ structures on dsAGP. Although dsAGP would not reflect the S2-bound form of AGP in the patient samples it could be used to relate the absorbance values obtained in the reversed lectin assay (FIG. 4C).

Intra-assay precision of the assay was determined by repeated analysis of a dsAGP sample on the same plate (96 wells). The coefficient of variation (CV) for intra-assay variation was 1.2% (not shown).

Inter-assay variability was determined by analyzing two HCC samples with intermediate and high absorbance values on three different plates. The CV for HCC (intermediate) and for HCC (high) was 2.8% and 5.0% respectively (not shown).

Example 4, Validation of Reversed S2-ELISA Using Patient Samples

Patient Samples

Plasma samples from 32 patients with liver cirrhosis, 28 patients with HCC and plasma samples from 32 patients with chronic hepatitis were included in the study. All included HCC samples were collected before treatment (Sorafenib treatment <1 month). Five of the HCC samples were from patients with recurrent HCC. None of the patients with liver cirrhosis had developed any signs of HCC 6 months after sampling. The patients with hepatitis were determined non-cirrhotic. A normal sample consisting of a pool of sera from blood donors with no signs of liver disease was used as a control.

Written consent was obtained from all patients and the study was approved by ethical committees at Linköping University and the Karolinska Institute.

Reversed S2-ELISA

The reversed S2-ELISA was performed as described above using plasma samples diluted 1:50 in PBS containing 1% BSA.

Analysis of Total AFP and AGP

Total AFP concentrations were determined in the clinical routine lab at Linköping University Hospital on a COBAS e602 analyser (Roche Diagnostics, Rotkreuz. Switzerland) and total AGP concentrations were determined in the clinical routine lab at Kalmar County Hospital on a BN ProSpec system (Siemens, Erlangen, Germany).

Statistical Analysis

All statistical analyses were performed using IBM SPSS 23. Statistical differences between groups were determined using Tukey's multiple comparison test in ANOVA. Binomial logistic regression was used to evaluate the combination of multiple markers. A p value of <0.05 was defined as being statistically significant. Receiver operating characteristics (ROC) curves and column scatter plots were generated with GraphPad Prism 5 (La Jolla, Calif.).

Results

The reversed S2-ELISA was used to determine the S2-bound AGP in patient sera from hepatitis patients, cirrhosis patients and HCC patients. There was a significant increase in S2-bound AGP in plasma from HCC patients compared to plasma from both hepatitis patients (p=0.001) and cirrhosis patients (p=0.005). There was no significant increase in the level of S2-bound AGP when comparing cirrhosis patients to hepatitis patients (FIG. 5A).

In the reversed S2-ELISA set-up, changes in concentration of AGP in the patient samples could potentially influence the detected glycosylation changes. Therefore, concentration of AGP was measured in all samples. AGP concentrations showed variation from 0.3 to 3.9 mg/ml. There was a significant increase in AGP concentration between HCC and hepatitis samples (p=0.008) and between HCC and cirrhosis samples (p=0.02) but no significant differences in AGP concentration between cirrhosis and hepatitis patients (FIG. 5B). However, there was no correlation between the S2-bound AGP signal and the AGP concentration (FIG. 6) indicating that concentration differences in AGP did not affect the diagnostic performance of the reversed S2-ELISA.

For comparison, the levels of AFP was also measured in the samples. The mean value of AFP was 5581 ng/ml in patients with HCC compared to 4 and 6 ng/ml in patients with cirrhosis and hepatitis, respectively. However these differences were not found to be significant (p=0.1, FIG. 5C).

Receiver operating characteristics (ROC) analysis was performed to determine the overall performance for each marker to differentiate between different patient populations. When differentiating HCC from hepatitis the area under curve (AUC) for S2-bound AGP was 0.94. Differentiation of HCC from cirrhosis gave an AUC of 0.77 (Table 1). AFP had a similar performance as S2-bound AGP with an AUC of 0.77 for differentiation of HCC and cirrhosis and an AUC of 0.82 for differentiation of HCC and hepatitis (Table 1). ROC analysis of AGP concentration showed that AGP concentration by itself had poor performance in differentiating HCC from Hepatitis (AUC 0.66) and HCC from cirrhosis (AUC 0.65).

Since there was an increase in the mean value of both S2-bound AGP, total AFP and total AGP when comparing HCC from cirrhosis patients, the performance of these markers was further analyzed using a combination of any two or all three markers using logistic regression analysis. A combination of all three markers showed the best differentiation between HCC and cirrhosis with an AUC of 0.86 and differentiation between HCC and hepatitis with an AUC of 0.95 (Table 1). The combination of S2-bound AGP with AFP and the combination of S2-bound AGP with AGP also gave better performance than any of the markers used alone (Table 1).

TABLE 1

| ROC-analysis (HCC vs. hepatitis and cirrhosis) | | |
|---|---|---|
| Marker | Hepatitis vs. HCC AUC (95% CI) | Cirrhosis vs. HCC AUC (95% CI) |
| AFP | 0.815 (0.699-0.93) | 0.77 (0.646-0.894) |
| AGP | 0.664 (0.522-0.806) | 0.653 (0.509-0.797) |
| S2-bound AGP | 0.941 (0.886-0.997) | 0.77 (0.644-0.893) |
| S2-bound AGP + AFP | 0.942 (0.887-0.997) | 0.826 (0.713-0.939) |
| S2-bound AGP + AGP | 0.949 (0.893-1.000) | 0.816 (0.706-0.926) |
| S2-bound AGP + AFP + AGP | 0.952 (0.896-1.000) | 0.864 (0.769-0.959) |

REFERENCES

1. Marrero J A. Hepatocellular carcinoma. Curr Opin Gastroenterol. 2006; 22: 248-253.
2. Perz J F, Armstrong G L, Farrington L A, Hutin Y J, Bell B P. The contributions of hepatitis B virus and hepatitis C virus infections to cirrhosis and primary liver cancer worldwide. J Hepatol. 2006; 45: 529-538.
3. Sarbah S A, Gramlich T, Younoszai A, et al. Risk factors for hepatocellular carcinoma in patients with cirrhosis. Dig Dis Sci. 2004; 49: 850-853.
4. Ertle J M, Heider D, Wichert M, et al. A combination of alpha-fetoprotein and des-gamma-carboxy prothrombin is superior in detection of hepatocellular carcinoma. Digestion. 2013; 87: 121-131.
5. Bruix J, Sherman M, American Association for the Study of Liver D. Management of hepatocellular carcinoma: an update. Hepatology. 2011; 53: 1020-1022.
6. Singal A, Volk M L, Waljee A, et al. Meta-analysis: surveillance with ultrasound for early-stage hepatocellular carcinoma in patients with cirrhosis. Aliment Pharmacol Ther. 2009; 30: 37-47.

7. Nakagawa T, Miyoshi E, Yakushijin T, et al. Glycomic analysis of alpha-fetoprotein L3 in hepatoma cell lines and hepatocellular carcinoma patients. J Proteome Res. 2008; 7: 2222-2233.
8. Ahn Y H, Shin P M, Kim Y S, et al. Quantitative analysis of aberrant protein glycosylation in liver cancer plasma by AAL-enrichment and MRM mass spectrometry. Analyst. 2013; 138: 6454-6462.
9. Comunale M A, Rodemich-Betesh L, Hafner J, et al. Linkage specific fucosylation of alpha-1-antitrypsin in liver cirrhosis and cancer patients: implications for a biomarker of hepatocellular carcinoma. PLoS One. 2010; 5: e12419.
10. Comunale M A, Wang M, Hafner J, et al. Identification and development of fucosylated glycoproteins as biomarkers of primary hepatocellular carcinoma. J Proteome Res. 2009; 8: 595-602.
11. Naitoh A, Aoyagi Y, Asakura H. Highly enhanced fucosylation of serum glycoproteins in patients with hepatocellular carcinoma. J Gastroenterol Hepatol. 1999; 14: 436-445.
12. Tanabe K, Deguchi A, Higashi M, et al. Outer arm fucosylation of N-glycans increases in sera of hepatocellular carcinoma patients. Biochem Biophys Res Commun. 2008; 374: 219-225.
13. Wang M, Long R E, Comunale M A, et al. Novel fucosylated biomarkers for the early detection of hepatocellular carcinoma. Cancer Epidemiol Biomarkers Prev. 2009; 18: 1914-1921.
14. Asazawa H, Kamada Y, Takeda Y, et al. Serum fucosylated haptoglobin in chronic liver diseases as a potential biomarker of hepatocellular carcinoma development. Clin Chem Lab Med. 2015; 53: 95-102.
15. Comunale M A, Wang M, Anbarasan N, et al. Total serum glycan analysis is superior to lectin-FLISA for the early detection of hepatocellular carcinoma. Proteomics Clin Appl. 2013; 7: 690-700.
16. Wimmerova M, Mitchell E, Sanchez J F, Gautier C, Imberty A. Crystal structure of fungal lectin: six-bladed beta-propeller fold and novel fucose recognition mode for *Aleuria aurantia* lectin. J Biol Chem. 2003; 278: 27059-27067.
17. Olausson J, Astrom E, Jonsson B H, Tibell L A, Pahlsson P. Production and characterization of a monomeric form and a single-site form of *Aleuria aurantia* lectin. Glycobiology. 2011; 21: 34-44.
18. Köhler G, Milstein C, "Continuous cultures of fused cells secreting antibody of predefined specificity", Nature. 1975 Aug. 7; 256(5517):495-7.
19. P. P. A. Marlies Leenaars, et al., "The production of Polyclonal Antibodies in Laboratory Animals: The Report and Recommendations of ECVAM Workshop 35", ATLA 27, 79-102, 1999.
20. Asao T, Yazawa S, Nishimura T, et al. Development of a novel system for mass spectrometric analysis of cancer-associated fucosylation in plasma alpha1-acid glycoprotein. Biomed Res Int. 2013; 2013: 834790.

The invention claimed is:

1. A method for detecting fucosylated alpha1-acid glycoprotein (AGP) that is associated with the presence of hepatocellular carcinoma (HCC) in a sample from a human individual, the method comprising:
providing a monovalent fucose-binding peptide having at least 80% identity to a peptide having an amino acid sequence according to SEQ ID NO: 1, immobilised on a solid phase, wherein the peptide differentially binds fucosylated AGP from a human subject with HCC compared to fucosylated AGP from a healthy human subject or a human subject with cirrhosis or hepatitis;
bringing the sample into contact with the immobilised fucose-binding peptide to bind fucosylated AGP that is associated with the presence of HCC; and
detecting fucosylated AGP that is associated with the presence of HCC bound to said fucose-binding peptide by bringing bound fucosylated AGP in contact with a first detection antibody capable of specific binding to a fucosylated AGP bound to said fucose-binding peptide.

2. The method according to claim 1, further comprising quantitating the amount of AGP in the sample.

3. The method according to claim 1, wherein the first detection antibody is conjugated to a detectable label.

4. A method for detecting fucosylated alpha1-acid glycoprotein (AGP) that is associated with the presence of hepatocellular carcinoma (HCC) in a sample from a human individual, the method comprising:
providing a monovalent fucose-binding peptide having at least 80% identity to a peptide having an amino acid sequence according to SEQ ID NO: 1, immobilised on a solid phase, wherein the peptide differentially binds fucosylated AGP from a human subject with HCC compared to fucosylated AGP from a healthy human subject or a human subject with cirrhosis or hepatitis;

bringing the sample into contact with the immobilised fucose-binding peptide to bind fucosylated AGP that is associated with the presence of HCC; and detecting fucosylated AGP that is associated with the presence of HCC bound to said fucose-binding peptide by bringing bound fucosylated AGP in contact with a first detection antibody capable of specific binding to a fucosylated AGP bound to said fucose-binding peptide and a second detection antibody capable of specific binding to the first detection antibody, and wherein the second detection antibody is conjugated to a detectable label.

5. The method according to claim 4, wherein the detectable label is selected from the group consisting of enzymes and fluorophores.

6. The method according to claim 4, wherein the first detection antibody is a polyclonal or monoclonal antibody.

7. The method according to claim 6, wherein the second detection antibody is a polyclonal or monoclonal antibody.

8. The method according to claim 1, wherein the AGP has a glycosylation pattern indicative of hepatocellular carcinoma.

9. A method for assessing a risk that a human individual suffers from hepatocellular carcinoma (HCC), the method comprising:
(a) quantitating fucosylated alpha1-acid glycoprotein (AGP) in a sample from said individual by:
(i) providing a monovalent fucose-binding peptide having at least 80% identity to a peptide having an amino acid sequence according to SEQ ID NO: 1, immobilised on a solid phase;
(ii) bringing the sample into contact with the immobilised fucose-binding peptide; and
(iii) detecting and quantitating fucosylated alpha1-acid glycoprotein (AGP) bound to said fucose-binding peptide by bringing bound fucosylated AGP in contact with a first detection antibody capable of specific binding to a fucosylated AGP bound to said fucose-binding peptide
(b) comparing the quantity of fucosylated AGP to a reference concentration derived from human individuals not suffering from HCC, and
(c) assessing a risk that the human individual suffers from HCC from the comparison, wherein an increased concentration of fucosylated AGP, as compared to the reference concentration derived from human individuals not suffering from HCC, indicates an increased risk that the individual suffers from HCC.

10. The method according to claim 9, further comprising measuring at least one of total AGP concentration and total alpha-fetoprotein (AFP) concentration in the sample.

11. The method according to claim 9, further comprising measuring total AGP concentration and total alpha-fetoprotein (AFP) concentration in the sample.

12. The method according to claim 9, wherein an increased concentration of fucosylated AGP, as compared to a reference concentration derived from human individuals suffering from liver cirrhosis and/or hepatitis, but not suffering from HCC, indicates an increased risk that the individual suffers from HCC.

13. The method of claim 1, wherein the monovalent fucose-binding peptide has at least 90% identity to a peptide having an amino acid sequence according to SEQ ID NO: 1.

14. The method of claim 1, wherein the monovalent fucose-binding peptide has 100% identity to a peptide having an amino acid sequence according to SEQ ID NO: 1.

15. The method according to claim 1, wherein the sample is a blood, serum, or plasma sample.

16. The method according to claim 15, wherein the sample is from a human subject suspected of suffering from hepatocellular carcinoma (HCC).

17. The method according to claim 1, wherein the first detection antibody is a polyclonal or monoclonal antibody.

18. The method of claim 4, wherein the monovalent fucose-binding peptide has at least 90% identity to a peptide having an amino acid sequence according to SEQ ID NO: 1.

19. The method of claim 4, wherein the monovalent fucose-binding peptide has 100% identity to a peptide having an amino acid sequence according to SEQ ID NO: 1.

20. The method according to claim 4, wherein the sample is a blood, serum, or plasma sample from a human subject suspected of suffering from hepatocellular carcinoma (HCC).

* * * * *

SEQUENCE LISTING

```
<160> NUMBER OF SEQ ID NOS: 3

<210> SEQ ID NO 1
<211> LENGTH: 114
<212> TYPE: PRT
<213> ORGANISM: Artificial Sequence
<220> FEATURE:
<223> OTHER INFORMATION: Lectin binding site 2 from A. aurantia lectin

<400> SEQUENCE: 1

Ser His Met Ser Gln Asn Val Ile Gly Glu Ala Lys Leu Phe Ser Pro
1               5                   10                  15

Leu Ala Ala Val Thr Trp Lys Ser Ala Gln Gly Ile Gln Ile Arg Val
                20                  25                  30

Tyr Cys Val Asn Lys Asp Asn Ile Leu Ser Glu Phe Val Tyr Asp Gly
            35                  40                  45

Ser Lys Trp Ile Thr Gly Gln Leu Gly Ser Val Gly Val Lys Val Gly
        50                  55                  60

Ser Asn Ser Lys Leu Ala Ala Leu Gln Trp Gly Gly Ser Glu Ser Ala
65                  70                  75                  80

Pro Pro Asn Ile Arg Val Tyr Tyr Gln Lys Ser Asn Gly Ser Gly Ser
                85                  90                  95

Ser Ile His Glu Tyr Val Trp Ser Gly Lys Trp Thr Ala Gly Ala Ser
            100                 105                 110

Phe Gly

<210> SEQ ID NO 2
<211> LENGTH: 201
<212> TYPE: PRT
<213> ORGANISM: Homo sapiens
<220> FEATURE:
<221> NAME/KEY: SIGNAL
```

```
<222> LOCATION: (1)..(19)

<400> SEQUENCE: 2

Met Ala Leu Ser Trp Val Leu Thr Val Leu Ser Leu Leu Pro Leu Leu
1               5                   10                  15

Glu Ala Gln Ile Pro Leu Cys Ala Asn Leu Val Pro Val Pro Ile Thr
            20                  25                  30

Asn Ala Thr Leu Asp Gln Ile Thr Gly Lys Trp Phe Tyr Ile Ala Ser
        35                  40                  45

Ala Phe Arg Asn Glu Glu Tyr Asn Lys Ser Val Gln Glu Ile Gln Ala
    50                  55                  60

Thr Phe Phe Tyr Phe Thr Pro Asn Lys Thr Glu Asp Thr Ile Phe Leu
65                  70                  75                  80

Arg Glu Tyr Gln Thr Arg Gln Asp Gln Cys Ile Tyr Asn Thr Thr Tyr
                85                  90                  95

Leu Asn Val Gln Arg Glu Asn Gly Thr Ile Ser Arg Tyr Val Gly Gly
            100                 105                 110

Gln Glu His Phe Ala His Leu Leu Ile Leu Arg Asp Thr Lys Thr Tyr
        115                 120                 125

Met Leu Ala Phe Asp Val Asn Asp Glu Lys Asn Trp Gly Leu Ser Val
    130                 135                 140

Tyr Ala Asp Lys Pro Glu Thr Thr Lys Glu Gln Leu Gly Glu Phe Tyr
145                 150                 155                 160

Glu Ala Leu Asp Cys Leu Arg Ile Pro Lys Ser Asp Val Val Tyr Thr
                165                 170                 175

Asp Trp Lys Lys Asp Lys Cys Glu Pro Leu Glu Lys Gln His Glu Lys
            180                 185                 190

Glu Arg Lys Gln Glu Glu Gly Glu Ser
        195                 200

<210> SEQ ID NO 3
<211> LENGTH: 19
<212> TYPE: PRT
<213> ORGANISM: Artificial Sequence
<220> FEATURE:
<223> OTHER INFORMATION: aa 183-201 of AGP

<400> SEQUENCE: 3

Cys Glu Pro Leu Glu Lys Gln His Glu Lys Glu Arg Lys Gln Glu Glu
1               5                   10                  15

Gly Glu Ser
```